United States Patent [19]

Hayes

[11] 4,095,471
[45] Jun. 20, 1978

[54] TIDAL SAMPLER

[75] Inventor: David W. Hayes, Aiken, S.C.

[73] Assignee: The United States of America as represented by the United States Department of Energy, Washington, D.C.

[21] Appl. No.: 784,403

[22] Filed: Apr. 4, 1977

[51] Int. Cl.² ............................................. G01N 1/14
[52] U.S. Cl. ................................................. 73/421 B
[58] Field of Search ........................ 73/421 R, 421 B; 417/119, 148

[56] References Cited

U.S. PATENT DOCUMENTS

| 1,625,519 | 4/1927 | Booth | 417/119 |
| 3,587,670 | 6/1971 | Brailsford | 73/421 B |

Primary Examiner—S. Clement Swisher
Attorney, Agent, or Firm—Dean E. Carlson; Allen F. Westerdahl

[57] ABSTRACT

An apparatus for pumping a sample of water or other liquid that uses the energy generated from the rise and fall of the liquid level to force a sample of the liquid into a collection vessel. A suction vessel and booster vessel with interconnecting tubing and check valves are responsive to an oscillating liquid level to pump a portion of said liquid into a collection vessel.

6 Claims, 1 Drawing Figure

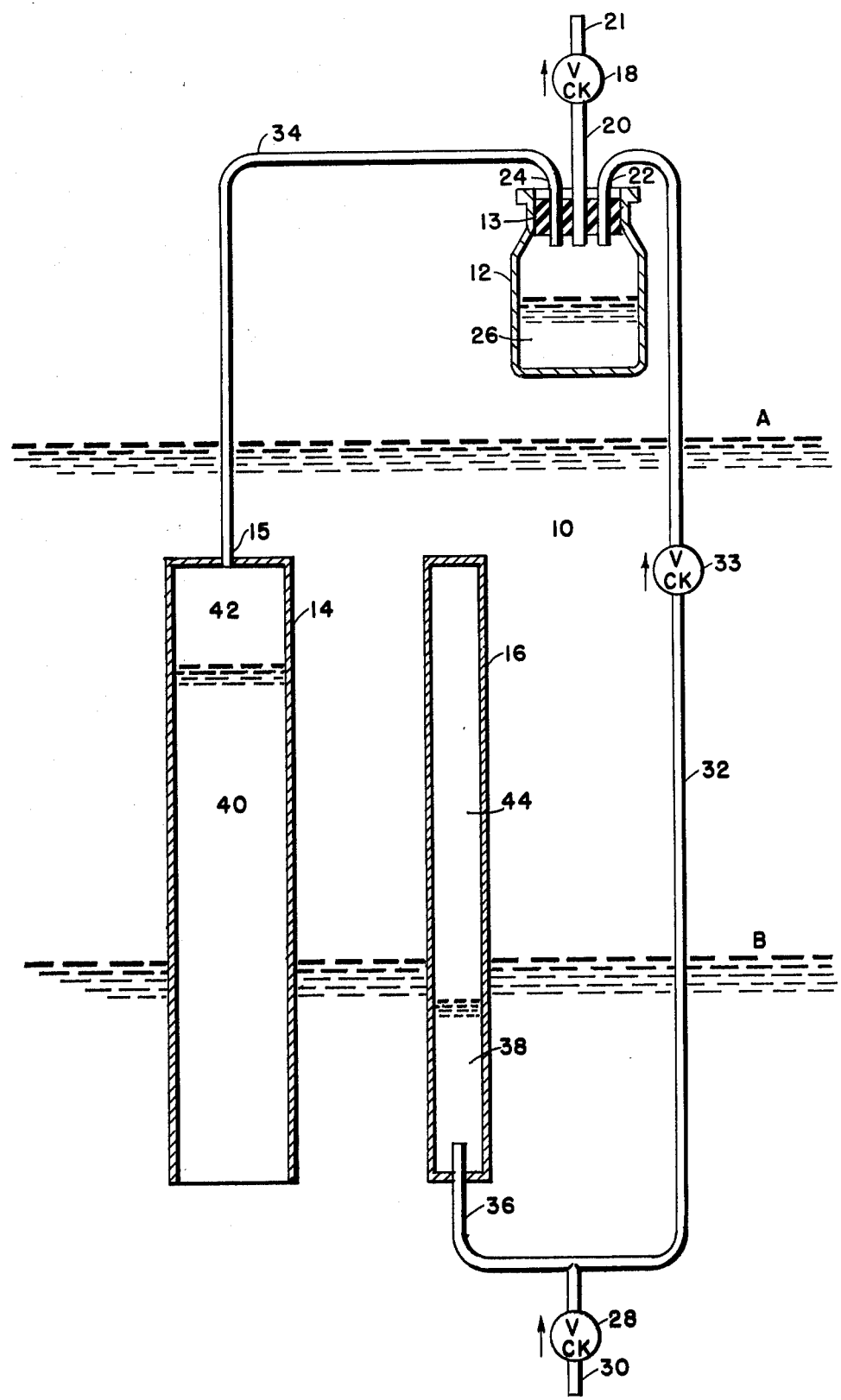

TIDAL SAMPLER

BACKGROUND OF THE INVENTION

This invention was made in the course of, or under, a contract with the U.S. Energy Research and Development Administration.

This invention relates to an apparatus for sampling liquids. In particular, for sampling liquids from a fluctuating or oscillating liquid source wherein the sample is pumped by energy of the oscillating liquid level. The invention is particularly useful to obtain environmental liquid samples in tidal waters.

Devices for automatic and continuous sampling water and other liquids in remote locations have generally depended on an external source of power, such as compressed gas or electrical energy. However, this type of sampler is not suitable for adverse or harsh environmental conditions or remote locations that require unattended operation for extended periods. In particular, battery powered samplers are susceptible to damaging corrosion in areas where oceanic waters have to be sampled and must be checked often to assure trouble-free operation.

SUMMARY OF THE INVENTION

Accordingly, it is the object of the present invention to provide a liquid sampler that requires no external power source other than an oscillating or fluctuating liquid level. It is also an object of the invention to provide a sampler of simple trouble-free construction that can operate unattended utilizing the energy from the rise and fall of oceanic tides.

In accordance with the present invention, there is provided a unique apparatus for pumping a sample of liquid from an oscillating liquid source, such as ocean tides, which comprises, in combination: (1) an enclosed collection vessel that includes a plurality of inlets and a check valve connected to an outlet open to the atmosphere; (2) a suction vessel submerged within the liquid to be sampled, being connected to the collection vessel; and (3) a booster vessel, also submerged in the liquid source, that includes a check valve with a sample inlet and with a connection to another inlet of the collection vessel. The suction vessel and the booster vessel are responsive to an oscillating liquid level, such as the rise and fall of ocean tides, so that a portion of the liquid is pumped into the collection vessel by the oscillation of said liquid level.

For its operation, the apparatus of the present invention depends entirely on oscillating rise and fall of the level of the liquid source. For optimum efficiency, the suction vessel described above must be completely submerged at the point of highest liquid level or high tide.

BRIEF DESCRIPTION OF THE DRAWING

The present invention is illustrated in the accompanying FIGURE which is a diagrammatic representation of a preferred embodiment of the apparatus disposed for operation in oceanic tidal waters.

DETAILED DESCRIPTION OF THE PREFERRED EMBODIMENT

Although the preferred embodiment of the present invention is described in an oceanic tidal environment, it will be recognized by those skilled in the art that the invention is also useful anywhere a liquid oscillates or fluctuates between generally known levels. Turning now to the accompanying FIGURE, the apparatus is shown disposed for use and operation in sampling tidal waters 10, with 10A representing high tide and 10B representing low or ebb tide with a collection vessel 12 disposed in a position for easy observation above high tide. The collection vessel 12 may be any suitable laboratory sample bottle including a stopper 13 with three inlets. These inlets include a delivery inlet 22, a suction inlet 24, and atmosphere check valve inlet 20. The atmosphere check valve inlet 20 is connected to a suitable check valve 18 with an outlet 21 to the atmosphere.

The submerged portion of the apparatus includes a suction vessel 14 with an open end that is inverted into the water to be sampled. The closed end of the suction vessel 14 has an outlet 15 that is connected by means of suction tube 34 to the suction inlet 24 on collection vessel 12. A booster vessel 16 is submerged adjacent to the suction vessel 14. The booster vessel 16 is an enclosed vessel having a booster inlet in the submerged end that is connected by means of booster inlet tube 36 to a delivery tube 32, then through a delivery check valve 33 to the delivery inlet 22 of the collection vessel 12. Between the booster inlet tube 36 and the delivery tube 32, a tee fitting provides connection for a sample check valve 28 and a sample inlet tube 30. The sample inlet tube 30 is disposed to admit a sample through the sample check valve 28 during the fluctuation of the tide as hereinafter described. The submerged vessels 14,16 with tubing connected to the collection vessel 12 may be made of any suitable material which will withstand corrosive ocean waters. It has been found that preferred material for the vessel and tubing are plastic, such as high molecular weight polyvinyl chloride, polypropylene or polyethylene. The check valves may be any suitable laboratory-type check valve also constructed of a non-corrosive material, such as glass, polyethylene or polypropylene. For example, glass ball check valves for laboratory use manufactured by Lab Glass, Inc. of Vineland, New Jersey, are suitable for use in the present invention.

It will be apparent that in order to operate properly, the suction vessel 14 and booster vessel 16 should be affixed to a suitable immovable object such as a piling or bridge support. No particular means of support is required except that at least a portion of both said vessels must be submerged at ebb tide.

In operation, the suction vessel 14 and the booster vessel 16 are lowered into the water or other liquid to be sampled with the above-described tubing and check valve 28, assuring that the length of these vessels is greater than the tidal or liquid level fluctuation range. For the most efficient operation, the suction vessel 14 and booster tube 16 must be completely submerged at high tide.

An exemplary description of the operation will start with the sampler apparatus just installed and the water level at ebb tide 10B. As the water level rises from ebb tide 10B to high tide 10A, the suction vessel 14 fills with water until the suction vessel water level 40 fills the air space 42 while exhausting air to the atmosphere through suction tube 34, collection vessel 12, and check valve 18. At the same time, sample check valve 28 opens admitting water through sample inlet 30 to delivery tube 32, also exhausting air through the collection vessel 12 and check valve 18, while pressurizing the air space 44 in the booster vessel 16 by a rise in booster vessel liquid level 38. The water level will, of course, rise to the same height in booster vessel 14 and delivery tube 32.

As the water recedes, i.e., the water level falls, check valves 18,28,33 close and the pressure in the collection vessel 12 is decreased by the suction created by drop in water level 40 of suction vessel 14. Pressure in the booster vessel 16 and the decreased pressure in the collection vessel 12 then forces water through inlet 36 and up the delivery tube 32 and into the collection vessel 12 to provide sample 26. Thus, the pumping action to deposit water in collection vessel 12 occurs during the falling tide and is completed at ebb tide 10B. After the tide has completed one cycle 10B to 10A to 10B, the apparatus will reach operating equilibrium, and water level 40 usually does not return to level 10B. Likewise, the water level in the delivery tube 32 does not reach the lowest level 10B. The water level in the delivery tube 32 is also controlled by delivery tube check valve 33 which provides for more efficient sample collection by preventing the water level in delivery tube 32 from dropping below the delivery inlet 22.

It will be recognized by those skilled in the art that the amount of sample collected may be controlled by and is proportional to the volume of the collection vessel and the area, length of the other vessels and tubing, and the capacity of the valves. The parameters may be adjusted as required to suit individual sampling requirements, such as the sampling time, volume of sample required, and the frequency and levels of the tides. Although this invention is described with reference to its preferred embodiment, it is contemplated that obvious modifications will occur to those skilled in the art and that such may be made without departing from the scope of this invention which is limited only as indicated in the appended claims.

What is claimed is:

1. An apparatus for pumping a sample of liquid from an oscillating liquid source which comprises in combination:
   a. an enclosed collection vessel including a plurality of inlets and a check valve having an outlet open to the atmosphere;
   b. suction means submersibly disposed in said liquid source and connected to one of the inlets of said collection vessel;
   c. booster means consisting essentially of an enclosed vessel including a check valve sample inlet and a delivery tube connected to another inlet of said collection vessel, said enclosed vessel being at least partially submerged in said liquid source when said source is at its lowest level; said suction means and said booster means being responsive to the oscillating level of said liquid source so as to pump a portion of said liquid into said collection vessel.

2. The apparatus of claim 1 wherein said oscillating liquid source is oceanic tidal waters.

3. The apparatus of claim 1 wherein said oscillating liquid source is wave action.

4. The apparatus of claim 1 wherein said suction means is a vessel with one end open and inverted in said liquid source.

5. The apparatus of claim 4 wherein said vessel is completely submerged in said liquid source when said liquid source is at its highest level and being at least partially submerged in said liquid source when said source is at its lowest level.

6. The apparatus of claim 1 wherein said delivery tube includes a check valve between said sample inlet check valve and said collection vessel whereby the delivery of liquid to said collection vessel is controlled.

* * * * *